(12) United States Patent
Artal Soriano et al.

(10) Patent No.: US 12,714,304 B2
(45) Date of Patent: Aug. 25, 2026

(54) OPHTHALMIC INSTRUMENT FOR MEASURING OPTICAL QUALITY OF EYE

(71) Applicant: AIER EYE HOSPITAL GROUP CO. LTD, Changsha (CN)

(72) Inventors: Pablo Luis Artal Soriano, Murcia (ES); Weizhong Lan, Changsha (CN); Enrique J Fernandez Martinez, Murcia (ES); Zhenghua Lin, Changsha (CN); Zhikuan Yang, Changsha (CN)

(73) Assignee: AIER EYE HOSPITAL GROUP CO. LTD, Changsha (CN)

( * ) Notice: Subject to any disclaimer, the term of this patent is extended or adjusted under 35 U.S.C. 154(b) by 717 days.

(21) Appl. No.: 17/920,791

(22) PCT Filed: Apr. 1, 2022

(86) PCT No.: PCT/CN2022/084759
§ 371 (c)(1),
(2) Date: Oct. 23, 2022

(87) PCT Pub. No.: WO2023/005252
PCT Pub. Date: Feb. 2, 2023

(65) Prior Publication Data

US 2024/0215824 A1 Jul. 4, 2024

(30) Foreign Application Priority Data

Jul. 29, 2021 (CN) ........................ 202110862091.X

(51) Int. Cl.
*A61B 3/10* (2006.01)
*A61B 3/00* (2006.01)
(Continued)

(52) U.S. Cl.
CPC .............. *A61B 3/12* (2013.01); *A61B 3/0091* (2013.01); *A61B 3/103* (2013.01); *A61B 3/13* (2013.01); *A61B 3/10* (2013.01)

(58) Field of Classification Search
CPC ......... A61B 3/12; A61B 3/0091; A61B 3/103; A61B 3/13; A61B 3/10
(Continued)

(56) References Cited

U.S. PATENT DOCUMENTS 6,050,687 A 4/2000 Bille et al.
2006/0114411 A1 6/2006 Wei et al.
(Continued)

FOREIGN PATENT DOCUMENTS

CN 101072534 A 11/2007
CN 101352333 A 1/2009
(Continued)

OTHER PUBLICATIONS

The European Search Report issued on Apr. 23, 2024 for EP22786741.3.

(Continued)

*Primary Examiner* — Mahidere S Sahle
(74) *Attorney, Agent, or Firm* — Yue (Robert) Xu; Apex Attorneys At Law, LLP

(57) ABSTRACT

An ophthalmic instrument for measuring optical quality of an eye is provided, including: a multi-element eyepiece and a rotatable mirror. A mirror surface of the rotatable mirror is optically conjugated with a first focal plane in an object space of the multi-element eyepiece through a first lens, to adjust an angle of light entering the eye. A focal point of the first lens is arranged in a virtual focal plane of the multi-element eyepiece. The multi-element eyepiece includes an eyepiece, a field lens and a second lens arranged in sequence. The field lens includes a third lens, a fourth lens
(Continued)

and a fifth lens arranged in sequence. The eyepiece, the third lens, the fourth lens and the fifth lens each is a positive lens, and the second lens is a negative lens.

10 Claims, 3 Drawing Sheets

(51) Int. Cl.

| | |
|---|---|
| ***A61B 3/103*** | (2006.01) |
| ***A61B 3/12*** | (2006.01) |
| ***A61B 3/13*** | (2006.01) |
| ***A61B 3/14*** | (2006.01) |

(58) Field of Classification Search

USPC .................................................. 351/205, 206

See application file for complete search history.

(56) References Cited

U.S. PATENT DOCUMENTS

| | | | |
|---|---|---|---|
| 2006/0221301 | A1 | 10/2006 | Hanebuchi |
| 2009/0030299 | A1 | 1/2009 | Naito |
| 2011/0211162 | A1 | 9/2011 | Thibos et al. |
| 2012/0307205 | A1 | 12/2012 | Zhou et al. |
| 2014/0354950 | A1 * | 12/2014 | Buckland ............... A61B 3/102 359/200.8 |
| 2022/0095913 | A1 | 3/2022 | Everett |
| 2022/0211265 | A1 | 7/2022 | Nakayama |
| 2022/0218199 | A1 | 7/2022 | Mizuta et al. |

FOREIGN PATENT DOCUMENTS

| | | | |
|---|---|---|---|
| CN | 102551654 | A | 7/2012 |
| CN | 103596488 | A | 2/2014 |
| CN | 110074753 | A | 8/2019 |
| CN | 111820864 | A | 10/2020 |
| CN | 112770664 | A | 5/2021 |
| CN | 113616152 | A | 11/2021 |
| JP | 2016123467 | A | 7/2016 |
| WO | 0160241 | A1 | 8/2001 |
| WO | 2021060203 | A1 | 4/2021 |
| WO | 2021065582 | A1 | 4/2021 |

OTHER PUBLICATIONS

International Search Report for PCT/CN2022/084759 mailed Jun. 28, 2022, ISA/CN.

The 1st Office Action dated Feb. 28, 2025 for the Chinese Patent Application No. CN202110862091.X. English Translation of the 1st Office Action Provided by http://globaldossier.uspto.gov.

* cited by examiner

OPHTHALMIC INSTRUMENT FOR MEASURING OPTICAL QUALITY OF EYE

The present application is the national phase of International Application No. PCT/CN2022/084759, titled "OPHTHALMIC INSTRUMENT FOR MEASURING OPTICAL QUALITY OF EYE", filed on Apr. 1, 2022, which claims priority to Chinese Patent Application No. 202110862091.X, titled "OPHTHALMIC INSTRUMENT FOR MEASURING OPTICAL QUALITY OF EYE", filed on Jul. 29, 2021 with the China National Intellectual Property Administration, which are incorporated herein by reference in their entireties.

FIELD

The present disclosure relates to the field of ophthalmic instruments for measuring optical quality, and in particular to an ophthalmic instrument for measuring optical quality of an eye.

BACKGROUND

Wavefront sensing technology has been widely used to obtain optical quality of an eye. A clinical diopter commonly used in clinical optometry may be directly obtained by estimating ocular aberrations. Defocus and astigmatism, commonly referred to as lower-order aberrations, constitute major factors to be considered in standard treatment regimens for visual aids, such as ophthalmic lenses, contact lenses, and other similar devices, in order to compensate for a refractive error of the eye.

The acquisition of human eye aberrations and off-axis refractive indexes, which affect most of everyday visual activities, has greatly improved in recent years. Off-axis optical quality of the eye has become a fundamental factor in the understanding of myopia and progress thereof in the field of vision science. Characterizing peripheral refractive distribution of the retinal by measuring a peripheral diopter opens a new window for understanding and studying the effectiveness of myopia treatments, with a main objective of preventing the development of myopia in children, ideally, even reversing the development, and inducing emmetropization of the eye.

Another interesting application for retrieving peripheral refraction is related to the ability to fabricate customized optical corrections, which may incorporate off-axis information to optimize vision across the field of view. It provides the feasibility of providing high-quality and customized corrections for the ophthalmology industry, which can eventually be applied to the technical fields of vision correction such as ophthalmic lenses, contact lenses, intraocular lenses, and corneal surgical ablation.

Typically, peripheral refraction of the retinal and aberrations are obtained by eye fixation on eccentric visual stimulation through known methods and instruments, such as aberrometers and autorefractometers, in order to detect the optical quality in a peripheral field of view, rather than on the optical axis of the eye. This completely depends on the ability of the patent to maintain a stable gaze. Different off-axis positions correspond to different gaze directions. As a gaze angle increases, the ability of the patent to maintain a stable gaze decreases, which makes the reliability of detection results not guaranteed. This is especially pronounced in the younger population (a main group in the development of myopia).

In U.S. Pat. No. 6,634,750B2, a wavefront is generated for a scanning beam by a telescopic relay. The wavefront propagates obliquely to a surface of a Shack-Hartmann wavefront sensor and changes continuously. The instrument is limited by an entrance diameter of a lens facing the wavefront sensor and by the size and optical power of an eyepiece. The limitation is directly related to a numerical aperture of the eyepiece. In practice, a scanned half-field is limited to around 15 degrees, which does not meet the requirements on characterizing peripheral refraction for practical monitoring of myopia progression.

U.S. Pat. No. 9,167,965B2 discloses an instrument for measuring off-axis optical quality of an eye, where a scanning relay moves around the head of the patent while allowing to be fixed in an open field of view, a sensing relay consists of a telescope causes a pupil of an eye to be conjugated to a surface of a Shack-Hartmann wavefront sensor through a periscope. Some disadvantages of the instrument lie in that an off-axis angle of the wavefront cannot be accurately estimated due to uncontrolled changes in a position of the patent. Additionally, mechanical rotation of the sensing relay in front of the eye imposes safety constraints on the patient and clinician. The mechanical rotation makes the measurement process relatively slow under a limitation by a speed at which the sensing relay rotates.

US patent US2011/0176113A1 discloses an optical instrument for measuring off-axis optical quality, where the combination of a scanning mirror and a number of prisms allows the retina to be illuminated with different degrees of eccentricity and a wavefront to be detected therefrom. For the optical instrument, a separate prism is required at a position corresponding to each field of view, which makes the optical instrument cumbersome and inflexible. Moreover, the position of the prism for each peripheral field of view is determined in advance, resulting in that the instrument is incapable of optical detection at other retinal sites. In practice, only a vertical direction and a horizontal direction can be scanned. Therefore, a gaze direction of the patient needs to be changed to observe other oblique positions in the field of view of the retina.

SUMMARY

The technical problem to be solved by the present disclosure is to provide an ophthalmic instrument for measuring optical quality of an eye. The ophthalmic instrument for measuring the optical quality of the eye allows to illuminate a retina with a wide range of eccentricity, being not limited to in a vertical or horizontal direction, and allows to measure the optical quality of the eye.

In order to solve the above technical problems, an ophthalmic instrument for measuring optical quality of an eye is provided according to the present disclosure. The ophthalmic instrument includes a multi-element eyepiece and a rotatable mirror, where a mirror surface of the rotatable mirror is optically conjugated with a first focal plane in an object space of the multi-element eyepiece through a first lens, to allow an angle of light entering the eye to be adjusted, where a focal point of the first lens is arranged in a virtual focal plane of the multi-element eyepiece, the multi-element eyepiece includes an eyepiece, a field lens and a second lens arranged in sequence, and the field lens includes a third lens, a fourth lens and a fifth lens arranged in sequence, where the eyepiece, the third lens, the fourth lens and the fifth lens each is a positive lens, and the second lens is a negative lens.

Optically, the ophthalmic instrument further includes a diopter detection system, where the diopter detection system includes a first lens group and a sensing device, and the sensing device is optically conjugated with the mirror surface of the rotatable mirror through the first lens group.

Optically, the ophthalmic instrument further includes a beacon system, where the beacon system includes a first light source and a first beam splitter, the first light source is arranged in a way that light emitted by the first light source is directed toward the mirror surface of the rotatable mirror through the first beam splitter, to allow an angle of the light entering the eye to be adjusted by rotating the mirror surface of the rotatable mirror, where the first beam splitter is arranged between the rotatable mirror and the first lens group, and is able to direct light emitted from the rotating mirror toward the first lens group.

Optically, the diopter detection system further includes a color filter element, and the color filter element is arranged in a light propagation path between the first lens group and the sensing device.

Optically, the ophthalmic instrument further includes a fixation system, where the fixation system includes a second light source, a sixth lens and a seventh lens, the sixth lens is arranged to be able to direct light emitted by the second light source toward the seventh lens, the seventh lens is arranged to be able to direct light projected by the sixth lens toward the multi-element eyepiece, and the seventh lens is movable along an optical axis of the seventh lens, to allow a distance between the seventh lens and the virtual focal plane of the multi-element eyepieces to be adjusted.

Optically, the fixation system further includes a second beam splitter and a third beam splitter, the second beam splitter is arranged to be able to direct light projected by the sixth lens toward the seventh lens, and the third beam splitter is arranged to be able to direct light projected by the seven lenses toward the multi-element eyepiece.

Optically, the third beam splitter is arranged between the second lens and the first lens.

Optically, the ophthalmic instrument further includes a pupil positioning system, where the pupil positioning system includes a third light source for illuminating a pupil plane of the eye, an eighth lens, and a positioning device, where the eighth lens is arranged to allow light emitted by an optical system of the eye to be directed toward the positioning device by passing through the multi-element eyepiece and the eighth lens in sequence.

Optically, the seventh lens is arranged in a light propagation path between the eighth lens and the multi-element eyepiece.

Optically, the pupil positioning system further includes a second lens group, the second lens group is arranged in a light propagation path between the eighth lens and the positioning device.

Through the above technical solutions, the present disclosure has the following advantageous effects.

A distance between the virtual focal plane of the multi-element eyepiece and the first lens is equal to a focal length of the first lens, so that the multi-element eyepiece and the first lens function as a telescope system, and light rays can exit from the first lens in parallel with each other and are reflected by the rotatable mirror to the diopter detection device to detect the diopter of the eye. In addition, by rotating the mirror surface of the rotatable mirror, incident light can be projected toward the first lens at different angles, and projected toward the multi-element eyepiece through the first lens. That is, the measuring light incidents from different heights of the multi-element eyepiece, which allows the light to enter the eye from different angles. Since the multi-element eyepiece includes the eyepiece, the third lens, the fourth lens, the fifth lens and the second lens arranged in sequence, the light is projected at different angles to the first focal plane in the object space of the multi-element eyepiece. Generally, the first focal plane coincides with the focal point in the object space of the eye, so that the incident light can generate light spots on the retina of the eye, so as to illuminate the retina with a wide range of eccentricity, thereby measuring the optical quality of the eye.

Other advantages of the present disclosure and the technical effects of the preferred embodiments will be further described in the following detailed description.

BRIEF DESCRIPTION OF THE DRAWINGS

The accompanying drawings are used to provide a further understanding of the present disclosure, and constitute a part of the specification, and together with the following detailed description, are used to explain the present disclosure, but do not constitute a limitation to the present disclosure. In the accompanying drawings.

DESCRIPTION OF REFERENCE NUMERALS

Figure 1:
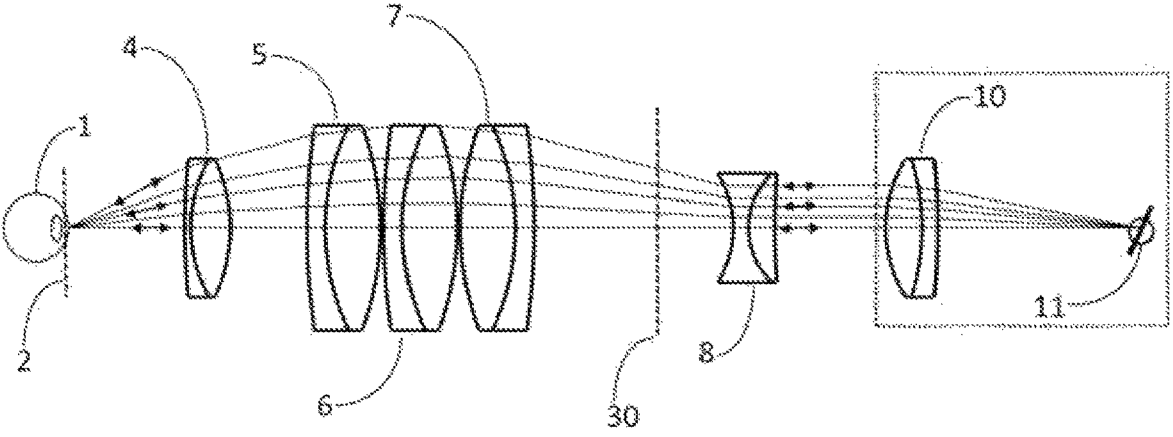
FIG. 1 is a schematic diagram illustrating the structure of an ophthalmic instrument for measuring optical quality of an eye according to a first embodiment of the present disclosure.

1 eye, 2 first focal plane, 3 system optical axis, 4 eyepiece, 5 third lens, 6 fourth lens, 7 fifth lens, 8 second lens, 9 third beam splitter, 10 first lens, 11 rotatable mirror, 12 first beam splitter, 13 first light source, 14 ninth lens, 15 first mirror, 16 tenth lens, 17 color filter element, 18 sensing device, 19 filter, 20 seventh lens, 21 second beam splitter, 22 eighth lens, 23 second mirror, 24 eleventh lens, 25 twelfth lens, 26 positioning device, 27 sixth lens, 28 focal plane of sixth lens, 29 second light source, 30 virtual focal plane, 35 multi-element eyepiece, 36 pupil plane, 37 third light source.

DETAILED DESCRIPTION OF THE EMBODIMENTS

Specific embodiments of the present disclosure will be illustrated in detail hereinafter in conjunction with the accompanying drawings. It should be understood that the specific embodiments described herein are only used to illustrate and explain the present disclosure, but not to limit the present disclosure.

In the description of the present disclosure, it should be noted that, unless otherwise expressly specified and limited, the terms "installation", "arrangement" and "connection" should be understood in a broad sense, for example, it may be understood a fixed connection, a detachable connection, or an integral connection; it may be a direct connection, or an indirect connection through an intermediate medium, and may be the internal communication between two elements or the interaction relationship between the two elements. For those of ordinary skill in the art, specific meanings of the above terms in the present disclosure can be understood according to specific situations.

In addition, the terms "first", "second", "third", "fourth", "fifth", "sixth", "seventh", "eighth", "ninth", "tenth", "eleventh" and "twelfth" are only used for the purpose of description, and cannot be understood as indicating or implying relative importance or indicating implicitly the number of technical features following them. Therefore, features defined by "first", "second", "third", "fourth", "fifth", "sixth", "seventh", "eighth", "ninth", "tenth", "eleventh" and "twelfth" may expressly or implicitly include one or more said features.

It should be understood that terms are described based on an orientation or a position relation shown in the drawings, and is only used for describing the present disclosure and simplifying the description, rather than instructing or implying that a device or element related to the terms has a specific orientation or is constructed and operated in a specific orientation. Therefore, the terms should be not construed as limitations to the present disclosure. Orientation terms of the present disclosure should be understood in conjunction with an actual installation state.

Reference is made to FIGS. 1 to 5. An ophthalmic instrument for measuring optical quality of an eye according to an embodiment of the present disclosure includes a multi-element eyepiece 35 and a rotatable mirror. A mirror surface of the rotatable mirror 11 is optically conjugated with a first focal plane 2 in an object space of the multi-element eyepiece 35 through a first lens 10, to adjust an angle of light entering the eye. A focal point of the first lens 10 is located on a virtual focal plane 30 of the multi-element eyepiece 35. The multi-element eyepiece 35 includes an eyepiece 4, a field lens and a second lens 8 arranged in sequence. The field lens includes a third lens 5, a fourth lens 6 and a fifth lens 7 arranged in sequence. The eyepiece 4, the third lens 5, the fourth lens 6 and the fifth lens 7 each is a positive lens, and the second lens 8 is a negative lens.

The ophthalmic instrument for measuring optical quality of an eye according to the present disclosure allows the optical quality of the eye to be detected objectively on a system optical axis at high eccentricity, thereby obtaining complete optical properties of the eye. The optical quality of the eye may be objectively estimated by measuring a wavefront generated from the eye. The multi-element eyepiece causes light to form a light spot on the retina, so that the wavefront may be considered as being generated by an emission point formed by a point light source projected on the retina. The wavefront may be analyzed when being emitted, or the wavefront may be converted into an intensity image by focusing it using a positive lens. The optical quality of the eye is estimated by analyzing the optical quality of the emission point on the retina. In order to completely describe the optical properties of the eye, the optical quality of emission points at different eccentricities covering all regions of interest may be analyzed and summarized.

In an embodiment, the multi-element eyepiece 35 is formed by different elements. FIG. 1 shows a structural design of the multi-element eyepiece 35. Referring to FIG. 1, the multi-element eyepiece 35 is includes an eyepiece 4, a third lens 5, a fourth lens 6, a fifth lens 7 and a second lens 8 arranged in sequence. The eyepiece 4 is arranged close to an eye of a patent. In a preferred embodiment, the eyepiece 4 is a biconvex lens with an entrance pupil diameter of 50 mm and a focal length of 100 mm, which minimizes the spherical aberration of the system. The third lens 5, the fourth lens 6 and the fifth lens 7 may be the same biconvex lenses. In a preferred embodiment, the third lens 5, the fourth lens 6 and the fifth lens 7 each is a biconvex lens with an entrance pupil diameter of 75 mm and a focal length of 200 mm. There is a free space of 1 mm between the third lens 5 and the fourth lens 6 and between the fourth lens 6 and the fifth lens 7. The third lens 5, the fourth lens 6 and the fifth lens 7 may be understood as field lenses, and combined arrangement of the third lens 5, the fourth lens 6 and the fifth lens 7 minimizes the optical aberration of the overall system. A lens operating near a focal plane of an objective lens is referred to as the field lens. The field lens changes a position of an imaging beam without changing the optical properties of an optical system. The second lens 8 is a negative lens. In a preferred embodiment, the second lens 8 is a biconcave lens with an entrance pupil diameter of 40 mm and a focal length of 60 mm. The first focal plane 2 of the multi-element eyepiece 35 is located in the object space of the multi-element eyepiece 35. The virtual focal plane 30 of the multi-element eyepiece 35 is located in an image space of the multi-element eyepiece 35. A geometric space in which light beams not transformed by the optical system are arranged is referred to as the object space, and a geometric space in which light beams transformed by the optical system are arranged is referred to as the image space. The virtual focal plane 30 of the multi-element eyepiece 35 is located between the fifth lens 7 and the second lens 8, and is spaced about 30 mm away from the second lens 8. The first lens 10 is arranged between the multi-element eyepiece 35 and the rotatable mirror 11. In a preferred embodiment, the first focal plane 2 in the object space of the multi-element eyepiece 35 is optically conjugated with the mirror surface of the rotatable mirror 11 through the first lens 10. The focal length of the first lens 10 is equal to a distance from the first lens 10 to the virtual focal plane 30 of the multi-element eyepiece 35. This structural design enables the multi-element eyepiece 35 and the first lens 10 to operate together as a telescope system, thus keeping the light collimated. The rotatable mirror 11 is configured to change a propagation angle of the light. When entering the first lens 10 at different heights away from the system optical axis 3, the light from the rotatable mirror 11 is projected to the first focal plane 2 at different angles through the multi-element eyepiece 35, which allows to generate scattered light spots on the retina of the patient at different eccentricities, covering all regions of interest on the retina. According to reversibility of an optical path, when the light is emitted from the retina of the patient and propagates toward the multi-element eyepiece 35, the light passes through the first lens 10 parallel to each other, and then be projected toward the rotatable mirror 11, regardless of the incident angle of the light at the eyepiece 4. The mirror surface of the rotatable mirror 11 is located at the focal plane of the first lens 10, so that the rotatable mirror 11 is optically conjugated with the first focal plane 2 of the multi-element eyepiece 35. In order to effectively couple the system to the eye 1 of the patient, the focal point of the eye 1 in the object space is located on the first focal plane 2 of the multi-element eyepiece 35. An angle at which measuring light enters the eye may be adjusted by rotating the rotatable mirror 11, so as to achieve a measurement of the peripheral refraction in two dimensions. Of course, when the focal point of the eye 1 in the object space is close to the first focal plane 2 of the multi-element eyepiece 35, the optical quality of the eye can also be detected.

It should be noted that the first lens 10, the second lens 8, the third lens 5, the fourth lens 6 and the fifth lens 7 are not limited to specific technical specifications shown in the above embodiments, such as the entrance pupil diameter, the focal length, the preparation materials and the distances among the first lens 10, the second lens 8, the third lens 5, the fourth lens 6 and the fifth lens 7. Any modifications to the technical specification are within scope of the present disclosure as long as the same effect is achieved.

Figure 2:
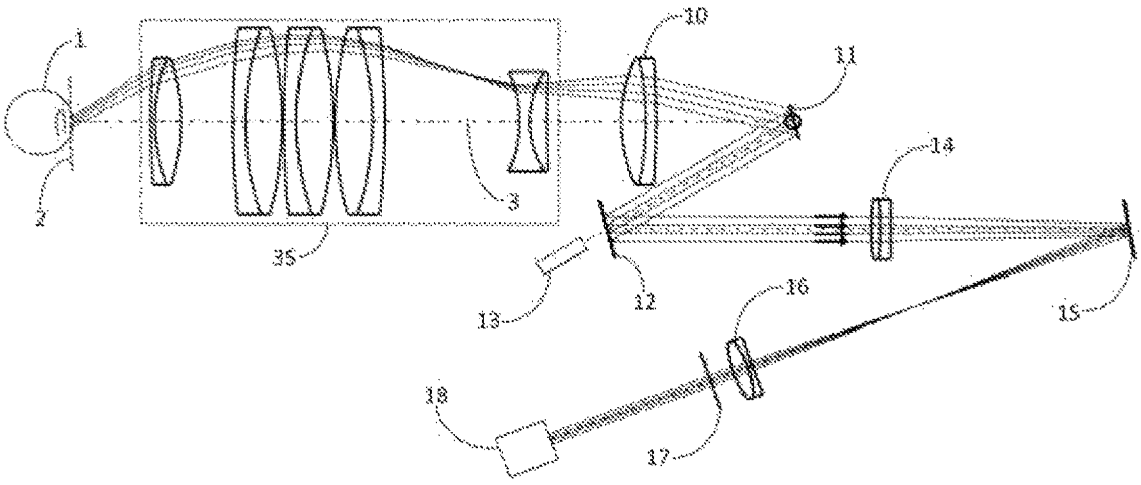
FIG. 2 is a schematic diagram illustrating the structure of an ophthalmic instrument for measuring optical quality of an eye according to a second embodiment of the present disclosure.
Figure 3:
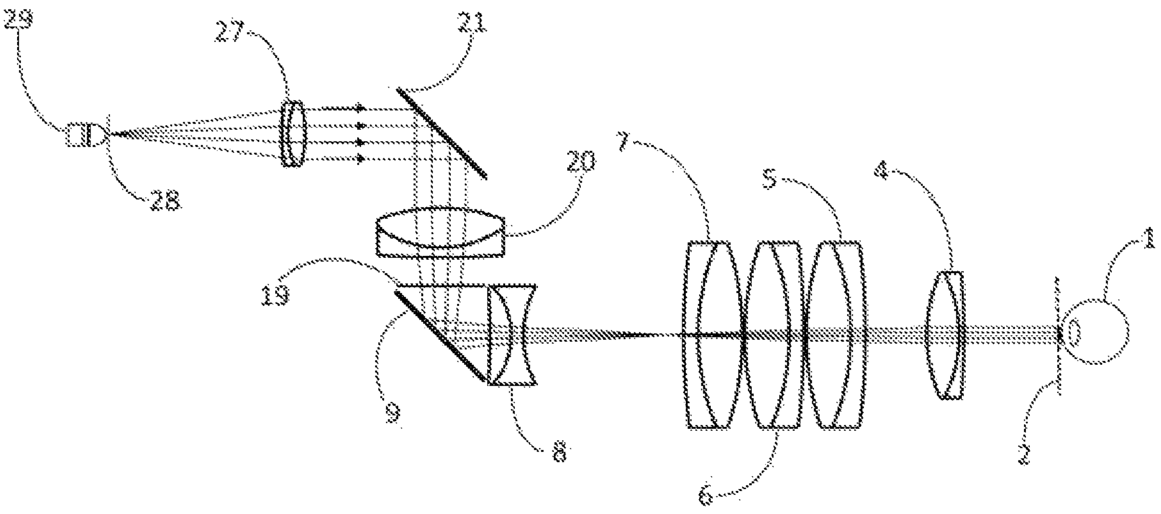
FIG. 3 is a schematic diagram illustrating the structure of an ophthalmic instrument for measuring optical quality of an eye according to a third embodiment of the present disclosure.

In actual operation, the rotatable mirror 11 directs light reflected and scattered by the eye to a diopter detection system. The diopter detection system receives light emitted by the eye 1 and obtains information about the optical quality of the eye 1 carried by the light. Reference is made to FIG. 2, the diopter detection system includes a first lens group and a sensing device 18. The sensing device 18 is optically conjugated with the mirror surface of the rotatable mirror 11 through the first lens group, and light reflected by the rotatable mirror 11 may be perceived by the sensing device 18 to obtain the information about the optical quality of the eye 1. In a preferred embodiment, the sensing device 18 may be a Shack-Hartmann wavefront sensor, or a system that produces a two-way image on a camera. That is, the sensing device 18 may be implemented by simply placing a camera sensor in the focal plane of the ninth lens 14 and before the sensing device 18.

In a preferred embodiment, a single rotatable mirror 11 is used to allow the light to be scanned to the eye 1 in any direction. However, a similar effect may be achieved by using two rotatable mirrors 11, with one of the two rotatable mirrors 11 operating in a direction perpendicular to the other of the two rotatable mirrors 11. The two rotatable mirrors 11 may be mounted close to each other in the system. Alternatively, the two rotatable mirrors 11 may be optically conjugated through a lens. The use of a single rotatable mirror 11 has significant advantages in terms of economy of elements, and simplicity and accuracy of control.

In order to generate a light spot on the retina of the patient, a beacon system may be included. The beacon system includes a first light source 13 and a first beam splitter 12. In a preferred embodiment, the first light source 13 may be a laser light source, and the laser is preferably light with a wavelength in a mid-infrared or near-infrared range of the spectrum, to increase safety and comfort of the patent. The light emitted by the first light source 13 is used as a laser beacon, and may be directed to the rotatable mirror 11 through the first beam splitter 12. The light is directed toward the first lens 10 by the rotatable mirror 11 and enters into the eye of the patent through the multi-element eyepiece 35. During the process of the laser beacon reaching the eye 1 from the laser 13, the rotatable mirror 11 changes the height of the light beam on the first lens 10, which finally changes the angle of the light entering the eye 1, forming the light spot on the retina. The first beam splitter 12 is arranged between the rotatable mirror 11 and the sensing device 18, to inversely scan a trajectory of the light from the retina of the patent. According to the reversibility of an optical path, during the process of the light emitting from the eye 1 and propagating toward the sensing device 18, the rotatable mirror 11 reflects the light toward the first beam splitter 12, and the first beam splitter 12 directs the light toward the first lens group. The light passes through the first lens group and is received by the sensing device 18 to obtain the diopter of the eye 1. The first lens group may include a ninth lens 14 and a tenth lens 16, so that the mirror surface of the rotatable mirror 11 is optically conjugated with the sensing device 18 through the ninth lens 14 and the tenth lens 16. In a preferred embodiment, the ninth lens 14 has a focal length of 200 mm, and the tenth lens 16 has a focal length of 80 mm. The focal plane of the ninth lens 14 is located on the rotatable mirror 11. The distance between the ninth lens 14 and the tenth lens 16 is equal to a sum of the focal length of the ninth lens 14 and the focal length of the tenth lens 16. The sensor surface of the sensing device 18 is located at the focal length of the tenth lens 16.

Further, a color filter element 17 may be provided to prevent light that does not come from the retina of the patient from reaching at the sensing device 18. The color filter element 17 is provided in the diopter detection system, for example, in a light propagation path between the first lens group and the sensing device 18, in a light propagation path between the ninth lens 14 and the tenth lens 16, or in a light propagation path between the first beam splitter 12 and the ninth lens 14, as long as the light that does not come from the retina of the patient is filtered. In a preferred embodiment, the color filter element 17 may be a color filter, an equivalent dichroic mirror or the like.

A first mirror 15 may further be provided in the diopter detection system to reduce mechanical extension of the entire system, that is, to reduce the size of the entire system. For example, the first mirror 15 is provided between the ninth lens 14 and the tenth lens 16, to reflect light emitted by the ninth lens 14 toward the tenth lens 16.

Since it is required to control the position of the light spot on the retina of the patient to generate a light beam carrying ocular aberration information, the eye 1 is required to be properly aligned and stabilized. A fixation system may be provided to allow the patient to focus on visual stimulation. In an embodiment, the fixation system includes a second light source 29, a sixth lens 27 and a seventh lens 20. The second light source 29 emits preferably light with a wavelength in the mid-infrared or near-infrared range of the spectrum to increase safety and comfort of the patient. The second light source 29 is arranged in the focal plane of the sixth lens 27. The sixth lens 27 may be a collimating lens. In a preferred embodiment, the sixth lens 27 may be a biconvex lens with an entrance pupil diameter of 25 mm and a focal length of 75 mm. The seventh lens 20 may be a positive lens with an entrance pupil diameter of 50 mm and a focal length of 100 mm. The seventh lens 20 may be mounted on a movable object stage, so that a distance between the seventh lens 20 and the virtual focus plane 30 of the multi-element eyepiece 35 may be adjusted accordingly. An interval between the sixth lens 27 and the seventh lens 20 affects light energy flux reaching the eye of the patient. Ideally, the light energy flux should be maintained as high as possible. In a front view position, the distance from the seventh lens 20 to the virtual focal plane 30 of the multi-element eyepiece 35 is equal to the focal length of the seventh lens 20. Therefore, the sixth lens 27 and the seventh lens 20 function as a telescope to allow the light to enter the seventh lens 20 with being collimated. When the eye exhibits myopia, the interval between the seventh lens 20 and the virtual focal plane 30 is required to be reduced to compensate for a refractive error. A displacement required to correct for a given refraction is inversely proportional to the square of the optical power of the multi-element eyepiece 35. When the eye exhibits hyperopia, the distance between the seventh lens 20 and the virtual focal plane 30 is required to be increased to correct for a refractive error. In this way, the light emitted by the second light source 29 is allowed to enter the multi-element eyepiece 35 by passing through the sixth lens 27 and the seventh lens 20 in sequence. Regardless of the refraction of the eye, the visual stimulation is focused on the retina of the patient, so as to avoid the blurring of the light, which makes it difficult for the patient to perceive the visual stimulation.

Further, a second beam splitter 21 may be provided between the sixth lens 27 and the seventh lens 20. The second beam splitter 21 is able to direct the light projected by the sixth lens 27 toward the seventh lens 20. A third beam splitter 9 may be provided between the seventh lens 20 and the multi-element eyepiece 35. The third beam splitter 9 is able to direct light projected by the seventh lens 20 toward the multi-element eyepiece 35. In a preferred embodiment, the third beam splitter 9 is arranged between the second lens 8 and the first lens 10. A filter 19 may further be provided between the seventh lens 20 and the third beam splitter 9. A distance from the seventh lens 20 to the filter 19 may be adjusted under action of the movable object stage.

The second light source 29 may be arranged on the system optical axis 3 or outside of the system optical axis 3. In a case that the second light source 29 is arranged outside of the system optical axis 3, a range of eccentricities measurable by the device is significantly increased. Optical elements of the fixation system allow for visual stimulation up to 20 degrees off the optical axis of the pupil at the entrance of the pupil of the eye, to maintain the light intensity. If the visual stimulation is applied beyond 20 degrees off the optical axis, the light intensity decreases. For example, if the multi-element eyepiece 35 scans in a total range of 70 degrees, or equivalent to 35 degrees per half, the extra 20 degrees will yield 35+20 degrees, which may be obtained in both halves. That is, a scanning range of 110 degrees is generated to detect the optical quality of the eye. The optical quality of any point on the retina may be measured from any direction due to the symmetry of the optical elements.

Figure 4:
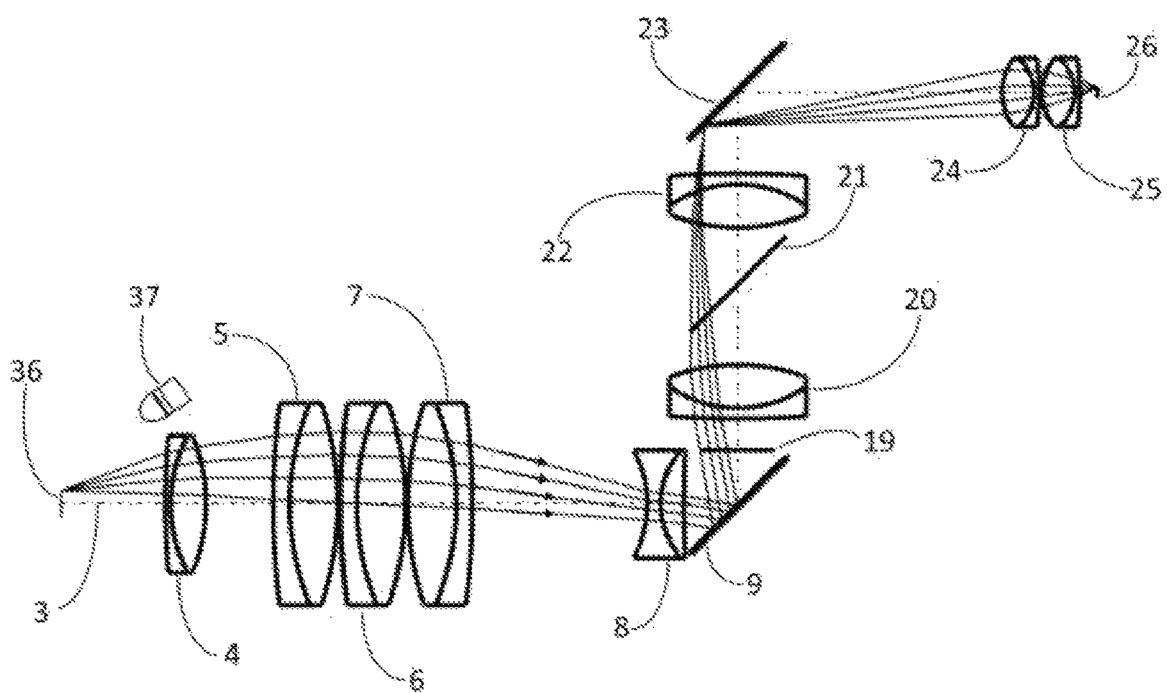
FIG. 4 is a schematic diagram illustrating the structure of an ophthalmic instrument for measuring optical quality of an eye according to a fourth embodiment of the present disclosure.

Typically, the eye 1 is required to be positioned prior to the inspection of the optical quality of the eye 1 using the sensing device 18. Referring to FIG. 4, a pupil positioning system may be provided. The pupil positioning system includes a third light source 37, an eighth lens 22 and a positioning device 26. The third light source 37 is used to illuminate a pupil plane 36 of the eye 1. In a preferred embodiment, the third light source 37 emits light with a wavelength in the mid-infrared or near-infrared range of spectrum. The pupil plane 36 is used as a positioning reference, which includes an iris, colored circular muscles surrounding the pupil, and the pupil itself. With the positioning device 26, the system allows images of the iris and the pupil to be displayed in near real-time to aid a user or a clinician in accurately positioning the eye 1 of the patient. In a preferred embodiment, the positioning device 26 may be a pupil camera. The third light source 37 emits light, illuminating the pupil plane 36 of the eye 1. Light reflected and scattered by the eye 1 is directed toward the third beam splitter 9 through the multi-element eyepiece 35. The third beam splitter 9 directs the light toward the seventh lens 20. Then the light is directed toward the eighth lens 22, and then focused on a sensor of the positioning device 26. The pupil plane 36 of the patent is positioned at the first focal plane 2 of the multi-element eyepiece 35 to image the iris and the pupil. A position at which the pupil plane 36 of the patient is clearly imaged is adjusted by moving the positioning device 26, which enables the positioning of the eye 1. Further, a second lens group may be further provided between the eighth lens 22 and the positioning device 26. The second lens group includes an eleventh lens 24 and a twelfth lens 25 arranged in sequence, so that the light focuses on a sensor of the pupil camera by passing through the seventh lens 20, the second beam splitter 21, the eighth lens 22, the eleventh lens 24 and the twelfth lens 25 in sequence. In a preferred embodiment, the eleventh lens 24 and the twelfth lens 25 form an objective lens, which minimizes the aberration. The eleventh lens 24 and the twelfth lens 25 may be the same lens, for example, a biconvex lens with an entrance pupil diameter of 25 mm and a focal length of 30 mm. The eleventh lens 24 and the twelfth lens 25 may be spaced from each other by 1 mm. Preferably, the eighth lens 22 is the same as the seventh lens 20, and the two are arranged in an oriented manner to reduce overall optical aberrations. For example, the eighth lens 22 is spaced from the seventh lens 20 by a distance of 51 mm. In addition, a second mirror 23 may further be provided between the eighth lens 22 and the second lens group to reduce the mechanical extension of the entire system, that is, to reduce the size of the pupil positioning system. Further, in a case that high-precision determination of off-axis optical quality is required, from an optical point of view, the focal point of the eye in the object space is required to be arranged in the first focal plane 2 of the multi-element eyepiece 35, and the focal point is located behind the pupil plane 36 of a normal eye. With the focal point of the eye 1 in the object space being arranged in the first focal plane 2 of the multi-element eyepiece 35, a off-center position of the light spot may be completely controlled, since any light entering the eye 1 toward the focal point of the eye 1 in the object space exits the system at the same angle relative to the system optical axis 3 and passes through a conjugated node in the image.

It should be noted that the eighth lens 22 and the seventh lens 20, the eleventh lens 24 and the twelfth lens 25, or the like may be different lenses, and the number of lenses may be changed, as long as corresponding functions can be achieved.

Figure 5:
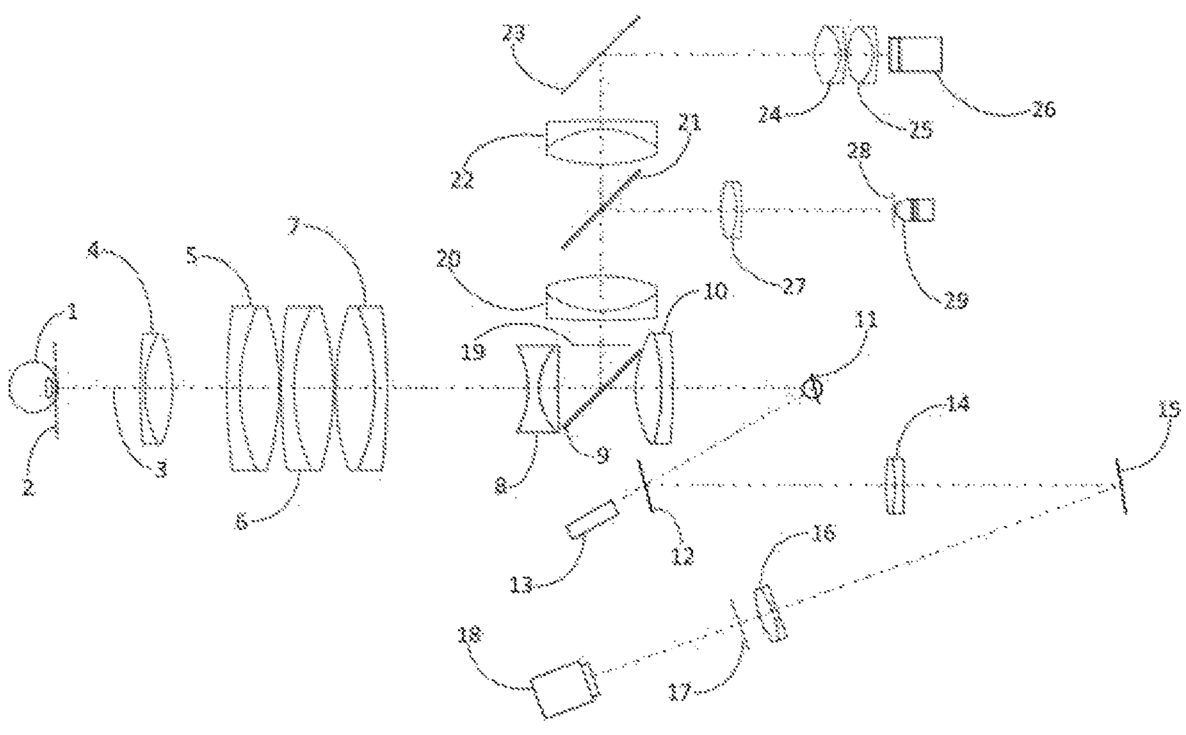
FIG. 5 is a schematic diagram illustrating the structure of an ophthalmic instrument for measuring optical quality of an eye according to a fifth embodiment of the present disclosure.

Reference is made to FIG. 5. In order to better understand the technical solution of the present disclosure, an operation process of the ophthalmic instrument for measuring optical quality of an eye according to the present disclosure will be described hereafter with reference to FIG. 5.

The third light source 37 is used to illuminate the pupil plane 36 of the eye 1, so that the pupil plane 36 of the patient is arranged in the first focal plane 2 of the multi-element eyepiece 35, to image the iris and the pupil. A position at which the pupil plane 36 of the patient is clearly imaged is adjusted by moving the positioning device 26, so as to position the eye with respect to the system optical axis 3 and the first focal plane 2 of the multi-element eyepiece 35.

By adjusting the distance between the seventh lens 20 and the filter 19, that is, adjusting the distance between the seventh lens 20 and the virtual focal plane 30, light emitted by the second light source 29 may enter into the multi-element eyepiece 35 by passing through the sixth lens 27, the second beam splitter 21, the seventh lens 20 and the third beam splitter 9 in sequence, enabling the visual stimulation to be focused on the retina of the patient.

The light emitted by the first light source 13 is used as a laser beacon. The light may be directed toward the rotatable mirror 11 through the first beam splitter 12, directed by the rotatable mirror 11 toward the first lens 10, and enters the eye of the patient through the multi-element eyepiece 35. During a process of the laser beacon reaching the eye 1 from the laser 13, the rotatable mirror 11 changes the height of the light beam on the first lens 10, which finally changes an angle of the light entering the eye 1, forming a light spot on the retina. According to the reversibility of an optical path, light reflected and scattered by the eye 1 passes through the multi-element eyepiece 35 and the first lens 10, and is directed toward the rotatable mirror 11. The rotatable mirror 11 directs light reflected and scattered by the eye toward the first beam splitter 12. The first beam splitter 12 then reflects the light toward the ninth lens 14, and then the light is reflected toward the tenth lens 16 by the first mirror 15, and is then focused on the sensor of the sensor device 18 through the color filter element 17 by the tenth lens 16, thereby detecting the optical quality of the eye 1.

By turning the rotatable mirror 11, the laser beacon may be scanned into the eye 1 at any eccentricity, thereby detecting a wavefront emerging from any point on the retina. The optical quality of the eye is objectively detected at a high eccentricity and on the optical axis, to obtain the complete optical properties of the eye.

Preferred embodiments of the present disclosure are described in detail above in conjunction with the accompanying drawings. However, the present disclosure is not limited to the details in the above embodiments. Various simple variants may be made to the technical solutions of the present disclosure within the scope of the technical concept of the present disclosure. These simple variants shall fall within the protection scope of the present disclosure.

In addition, it should be noted that various technical features described in the above embodiments may be combined in any appropriate manner if there is no contradiction. In order to avoid unnecessary repetition, various possible combinations are not described in the present disclosure.

In addition, various embodiments of the present disclosure may also be combined arbitrarily without violating the idea of the present disclosure, and the combinations shall also be regarded as being disclosed in the present disclosure.

The invention claimed is:

1. An ophthalmic instrument for measuring optical quality of an eye, comprising:

a multi-element eyepiece and a rotatable mirror, wherein a mirror surface of the rotatable mirror is optically conjugated with a first focal plane in an object space of the multi-element eyepiece through a first lens, to adjust an angle of light entering the eye, wherein the first lens is arranged between the multi-element eyepiece and the rotatable mirror, and a focal point of the first lens is arranged in a virtual focal plane in an image space of the multi-element eyepiece, such that light incident to or emitted from the first lens is collimated and the multi-element eyepiece and the first lens function as a telescope system, and the multi-element eyepiece comprises an eyepiece, a field lens and a second lens arranged in sequence, and the field lens comprises a third lens a fourth lens and a fifth lens arranged in sequence, wherein the eyepiece, the third lens, the fourth lens and the fifth lens each is a positive lens, and the second lens is a negative lens.

2. The ophthalmic instrument for measuring optical quality of an eye according to claim 1, further comprising a diopter detection system, wherein the diopter detection system comprises a first lens group and a sensing device, and the sensing device is optically conjugated with the mirror surface of the rotatable mirror through the first lens group.

3. The ophthalmic instrument for measuring optical quality of an eye according to claim 2, further comprising a beacon system, wherein the beacon system comprises a first light source and a first beam splitter, the first light source is arranged in a way that light emitted by the first light source is directed toward the mirror surface of the rotatable mirror through the first beam splitter, to adjust an angle of the light entering the eye by rotating the mirror surface of the rotatable mirror, the first beam splitter is arranged between the rotatable mirror and the first lens group, to direct light emitted from the rotating mirror toward the first lens group.

4. The ophthalmic instrument for measuring optical quality of an eye according to claim 2, wherein the diopter detection system further comprises a color filter element arranged in a light propagation path between the first lens group and the sensing device.

5. The ophthalmic instrument for measuring optical quality of an eye according to claim 1, further comprising a fixation system, wherein the fixation system comprises a second light source, a sixth lens and a seventh lens, the sixth lens is configured to direct light emitted by the second light source toward the seventh lens, the seventh lens is configured to direct light projected by the sixth lens toward the multi-element eyepiece, and the seventh lens is movable along an optical axis of the seventh lens, to allow a distance between the seventh lens and the virtual focal plane of the multi-element eyepieces to be adjusted.

6. The ophthalmic instrument for measuring optical quality of an eye according to claim 5, wherein the fixation system further comprises a second beam splitter and a third beam splitter, the second beam splitter is configured to direct light projected by the sixth lens toward the seventh lens, and the third beam splitter is configured to direct light projected by the seven lenses toward the multi-element eyepiece.

7. The ophthalmic instrument for measuring optical quality of an eye according to claim 6, wherein the third beam splitter is arranged between the second lens and the first lens.

8. The ophthalmic instrument for measuring optical quality of an eye according to claim 6, further comprising a pupil positioning system, wherein the pupil positioning system comprises a third light source for illuminating a pupil plane of the eye, an eighth lens, and a positioning device, wherein the eighth lens is configured to direct light emitted by an optical system of the eye toward the positioning device by passing through the multi-element eyepiece and the eighth lens in sequence.

9. The ophthalmic instrument for measuring optical quality of an eye according to claim 8, wherein the seventh lens is arranged in a light propagation path between the eighth lens and the multi-element eyepiece.

10. The ophthalmic instrument for measuring optical quality of an eye according to claim 8, wherein the pupil positioning system further comprises a second lens group, the second lens group is arranged in a light propagation path between the eighth lens and the positioning device.

* * * * *